(12) United States Patent
Dormer et al.

(10) Patent No.: US 10,238,663 B2
(45) Date of Patent: Mar. 26, 2019

(54) EXTENDED-RELEASE DRUG DELIVERY COMPOSITIONS

(71) Applicant: ORBIS BIOSCIENCES, INC., Lenexa, KS (US)

(72) Inventors: Nathan Dormer, Mission, KS (US); Cory Berkland, Lawrence, KS (US)

(73) Assignee: ORBIS BIOSCIENCES, INC., Kansas City, KS (US)

( * ) Notice: Subject to any disclaimer, the term of this patent is extended or adjusted under 35 U.S.C. 154(b) by 0 days.

(21) Appl. No.: 15/643,857

(22) Filed: Jul. 7, 2017

(65) Prior Publication Data

US 2017/0304320 A1 Oct. 26, 2017

Related U.S. Application Data

(63) Continuation of application No. 14/738,174, filed on Jun. 12, 2015.

(60) Provisional application No. 62/011,380, filed on Jun. 12, 2014.

(51) Int. Cl.

| | |
|---|---|
| *A61K 31/573* | (2006.01) |
| *A61K 31/711* | (2006.01) |
| *A61K 9/16* | (2006.01) |
| *A61K 31/43* | (2006.01) |
| *A61K 38/38* | (2006.01) |
| *A61K 31/713* | (2006.01) |
| *A61K 9/00* | (2006.01) |
| *A61K 47/10* | (2017.01) |
| *A61K 47/26* | (2006.01) |
| *A61K 47/32* | (2006.01) |
| *A61K 47/38* | (2006.01) |
| *A61K 9/10* | (2006.01) |

(52) U.S. Cl.
CPC .......... *A61K 31/573* (2013.01); *A61K 9/0019* (2013.01); *A61K 9/0046* (2013.01); *A61K 9/10* (2013.01); *A61K 9/1635* (2013.01); *A61K 9/1647* (2013.01); *A61K 31/43* (2013.01); *A61K 31/711* (2013.01); *A61K 31/713* (2013.01); *A61K 38/38* (2013.01); *A61K 47/10* (2013.01); *A61K 47/26* (2013.01); *A61K 47/32* (2013.01); *A61K 47/38* (2013.01)

(58) Field of Classification Search
CPC .... A61K 31/573; A61K 31/43; A61K 31/713; A61K 31/711; A61K 38/38; A61K 9/1635; A61K 9/1647; A61K 9/0019; A61K 9/0046; A61K 47/10; A61K 47/26; A61K 47/32; A61K 47/38; A61K 9/10
See application file for complete search history.

(56) References Cited

U.S. PATENT DOCUMENTS

| | | | | |
|---|---|---|---|---|
| 5,843,930 | A * | 12/1998 | Purwar ................. | A61K 9/0046 424/437 |
| 2009/0246255 | A1* | 10/2009 | Meyer .................. | A61K 9/0046 424/437 |
| 2012/0269866 | A1* | 10/2012 | Ali ....................... | A61K 9/0065 424/400 |

OTHER PUBLICATIONS

Selvol Polyvinyl Alcohol Product Brochure.
Selvol Polyvinyl Alcohol Solution Preparation Guidelines.
Bercea et al., "In situ gelation of aqueous solutions of entangled poly(vinyl alcohol)" Soft Matter, 2013, 9, 1244-1253.

* cited by examiner

*Primary Examiner* — Johann R Richter
*Assistant Examiner* — Genevieve S Alley
(74) *Attorney, Agent, or Firm* — Robert R. Riddle; Matthew S. Gibson; Reed Smith LLP

(57) ABSTRACT

An extended-release drug delivery composition and method of administering the same is provided. The composition comprises microspheres loaded with a biologically-active agent and suspended in a soluble polymer capable of forming a film upon injection onto a biological surface.

12 Claims, 10 Drawing Sheets

(9 of 10 Drawing Sheet(s) Filed in Color)

EXTENDED-RELEASE DRUG DELIVERY COMPOSITIONS

CROSS-REFERENCE TO RELATED APPLICATIONS

The present application continuation of U.S. application Ser. No. 14/738,174 filed on Jun. 12, 2015, which claims priority to U.S. Provisional Application No. 62/011,380 filed on Jun. 12, 2014, which is incorporated herein by reference in its entirety.

STATEMENT OF GOVERNMENT INTEREST

This invention was made with government support under Grant No. 1R43DC012749-01 awarded by National Institutes of Health. The government has certain rights in the invention.

BACKGROUND

One of the challenges in drug delivery is the ability to target the treatment to a particular area of the body or a particular biological tissue and maintain delivery at the area or tissue. In most instances, repetitive treatments are needed over the course of days to weeks in order to maintain the necessary therapeutic level of an active agent. Simply stated, this approach is inconvenient and costly.

For example, sudden sensorineural hearing loss (SSNHL) is a disease that attacks 4,000 Americans annually and is characterized by near complete hearing loss in as little as a few hours. The most efficacious treatment for SSNHL consists of frequent injections of an anti-inflammatory steroid into the middle ear, which diffuses into the inner ear via the round-window membrane (RWM). The invasive nature of these injections, especially if delivery is desired directly on the surface of the RWM, results in low patient compliance and a loss of efficacy. Thus, SSNHL patients and patients having other conditions that require a localized long-term treatment protocol would benefit from a drug delivery platform that permits the use of a single injection while providing an extended-release profile of the therapeutic agent.

SUMMARY

The present disclosure relates to an extended-release drug delivery platform. In one embodiment, an extended-release therapeutic composition is provided. The composition comprises a film forming agent and a biologically active agent. The film forming agent can be a soluble polymer, whether in water or some other solvent, including, but not limited to, ethanol, benzyl alcohol, or ethyl acetate. Examples of suitable polymers include, but are not limited to polyvinyl alcohol (PVA), polyvinyl acetate (PVAc), alginate, polyethylene glycol (PEG), hydroxypropyl methyl cellulose (HPMC), polyvinyl pyrrolidone (PVP), eudragits, collagen, and gelatin. The biologically active agent can be, for example, a therapeutic compound or a diagnostic agent. The biologically active agent can be loaded in a plurality of microspheres or microcapsules. The composition may further comprise a surfactant. The surfactant can be, for example, polysorbate or sorbitan laurate.

In another embodiment, a single-injection method for administration of a composition to a target tissue is provided. The method comprises the step of injecting a composition onto a biological tissue of a subject, wherein the composition comprises a film forming agent and a biologically active agent. In one instance, the biological tissue is the round window membrane of the inner ear and the step of injecting includes the use of an intratympanic injection. The method may further comprise allowing the composition to form a film on the biological tissue by maintaining the subject in a position to facilitate retention of the composition on the biological tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Some specific example embodiments of the disclosure may be understood by referring, in part, to the following description and the accompanying drawings.

DESCRIPTION

Figure 1:
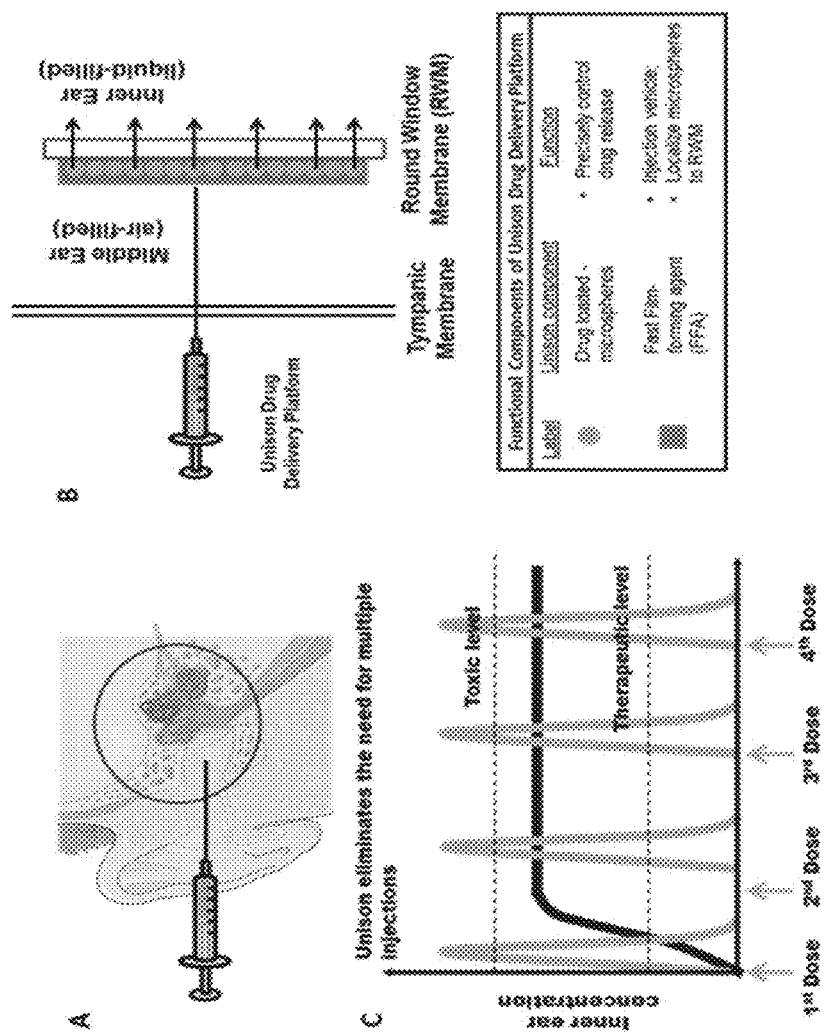
FIG. 1 describes (A) the process of intratympanic injection, whereas the film forming formulation is deposited directly on the RWM, (B) illustrates the attachment of the drug delivery system, in this instance with microspheres, to the RWM, and (C) illustrates the replacement of multiple therapeutic injections with a single injection film forming drug delivery system.

The present disclosure provides an extended release drug delivery platform using a fast film forming agent (FFA). The FFA can be applied to a surface of a target tissue where it is allowed to form a film. The film retains a biologically-active agent that is then released over a desired period of time and in many instances, over weeks. This provides the advantage of maintaining a proper localization for the treatment and also permits a fine tuning of the release profile. In one embodiment, the FFA can be used to deliver drug-loaded microcapsules or microspheres to the round membrane window via an intratynpanic injection thereby eliminating the need for multiple, painful injections while providing for more predictable drug levels within the inner ear perilymph for treatment of inner ear disorders such as SSNHL. To this end, FIG. 1 provides a representation of the intratympanic injection procedure in relationship to the anatomy of the ear (panel A). Panel B of FIG. 1 depicts intratympanic injection of drug-loaded microspheres (orange circles) which localize to the round window membrane (RWM) using the present FFA composition (green squares). Using the present FFA composition, a delivery system for maintaining localization of a therapeutic agent to the RWM with a single injection is possible, in contrast to multiple injections. Thus, the present disclosure provides compositions comprising the FFA and methods of using the same to provide an extended-release therapy for treatment of various disorders that require long-term localized treatment, including inner ear disorders.

In one embodiment, a composition that provides an extended-release profile is provided. The composition comprises a film forming agent and a biologically active agent.

The film-forming agent (FFA) is a means for forming a film on a biological tissue of a subject (also referred to herein as "film forming means" or "FFA means"). The film forming means of the present disclosure is capable of: (i) serving as the injectable carrier for a biologically-active agent, such as drug-loaded microspheres or microcapsules, and (ii) adhering the biologically-active agent to a target membrane, biological tissue, or surface, such as the round window membrane (RWM) of the inner ear, for an extended period of time, for example 20 to 35 days. The FFA means is comprised of Generally Accepted as Safe (GRAS) materials and is readily soluble in water or other appropriate solvents, allowing it to be delivered in a dry powder syringe for resuspension immediately prior to use. The FFA means, in one embodiment, comprise a soluble polymer such as polyvinyl alcohol (PVA), polyvinyl acetate (PVAc), alginate, polyethylene glycol (PEG), hydroxypropyl methyl cellulose (HPMC), polyvinyl pyrrolidone (PVP), eudragits, collagen, and gelatin. For example, in one embodiment, the film forming means is PVA having a molecular weight range of 20,000 to 30,000 and in some instances may by hydrolyzed (e.g., 88% hydrolyzed).

In certain embodiments, the film forming means may comprise 0.5-10% w/v of the composition. However, it should be understood that the film forming means may be formulated at different percentages based on the particular polymer employed. For example, a FFA means comprising PEG could account for 60-90% w/v of the composition.

The film forming means further comprises a carrier liquid. The carrier liquid utilized is dependent on the polymer or other substance used for the film forming agent and may be a water or a solvent. Furthermore, the carrier liquid should possess the ability to evaporate at physiological temperatures, such as 37° C. Thus, the excess carrier liquid that does not form part of the film will evaporate quickly. The carrier liquid of the film forming means includes, for example, water, ethanol, benzyl alcohol, and ethyl acetate.

The composition may further comprise a number of different excipients including a surfactant, a stabilizer, a release modifier, or a densifier. For example, a surfactant is used in certain embodiments of the present composition based on the solubility of the biologically-active agent. In the instance the biologically active agent is hydrophobic, polysorbate can be used as the surfactant. However, sorbitan laurate can be used in the instance the biologically-active agent is hydrophilic. The surfactant can be polysorbate 20, polysorbate 60, or polysorbate 80 based on the desired release profiles of the biologically-active agent. The excipient may comprise approximately 0.1%-10% w/v of the composition, and in some instance, 0.5-5% w/v of the composition.

Upon injection at the target surface, the film forming means generally forms a film upon evaporation of the water or solvent content of the composition which, in some instances, will occur in about 20-50 minutes post-injection. It should be understood that use of the FFA means to deliver biologically-active agents to the inner ear is just one embodiment of the technology and the FFA means could be used in a variety of other applications. Referring now to panel B of FIG. 1, examples of target biological surfaces or tissues in which the FFA means is preferable are those surfaces, tissues, or membranes that provide a barrier between a predominately non-fluid or air-filled cavity and a fluid-rich or tissue-dense region, such surfaces referred to herein as biological barrier structures. Examples of biological barrier structures are the round membrane window of the inner ear or the external surface of a nasal polyp. In these instances, the FFA means is applied to the side of the membrane, tissue, or surface exposed to the non-fluid or air-filled cavity which permits the FFA means to dry and form a film on the surface. The liquid or tissue on the other side of the membrane, surface, or tissue facilitates diffusion of the biologically-active agent from the FFA means into the fluid-filled area thereby targeting the therapy or diagnostic to the target region.

The biologically-active agent may comprise a therapeutic or diagnostic compound and thus may be, for example, a steroid, antibody, peptide, nucleic acid, antioxidant, chemical, small molecule, and other similar compounds. In one embodiment, the biologically-active agent is betamethasone, dexamethasone, or penicilin.

The biologically-active agent can be formulated as nanoparticle or microsphere. For example, the biologically active compound may be fabricated using the Precision Particle Formation (PPF) method as described in U.S. Pat. Nos. 6,669,961, 7,368,130, and 7,309,500, all of which are incorporated by reference herein in their entireties. Briefly, in this method, a drug-matrix solution is sprayed through a nozzle with (i) vibrational excitation to produce uniform droplets, and (ii) an annular, non-solvent carrier stream to reduce the diameter of the exiting jet. The microspheres can be formed of poly (D,L-lactic-co-glycolic acid) (PLGA), poly(lactic acid) (PLA), poly(glycolic acid) (PGA), poly(caprolactone) (PCL), poly(ethylene glycol) (PEG), poly(vinyl acetate) (PVAc), ethyl cellulose, or similar biodegradable polymers compatible with precision particle fabrication technology as described in U.S. Pat. Nos. 6,669,961, 7,368,130, and 7,309,500.

Alternatively, in certain other embodiments, rather than comprising a homogenous mixture of the biologically-active agent and polymer materials, the microsphere may comprise a hydrophobic matrix layer and a core, wherein the biologically-active agent is dispersed within the core and is surround by the hydrophobic matrix layer. These microspheres may also be fabricated using the PPF method referred to above. The hydrophobic matrix may be a hydrophobic wax material, a lipid material, a glycol polymer, or a combination thereof. In certain embodiments, suitable hydrophobic matrix materials have a melting point at or above about 45° C. and a viscosity when melted sufficient to allow spraying.

Suitable lipid materials should be solid at room temperature and have a melting temperature at or above about 45° C. Examples of suitable lipid materials include, but are not limited to, glycerol fatty acid esters, such as triacylglycerols (e.g., tripalmitin, tristearin, glyceryl trilaurate, coconut oil), hydrogenated fats, ceramides, and organic esters from and/ or derived from plants, animals, minerals.

Suitable glycol polymers should be solid at room temperature and have a melting temperature at or above about 45° C. Examples of suitable glycol polymers include, but are not limited to, high molecular weight glycols (e.g., polyethylene glycol with a minimum of 20 repeating units), cellulose ethers (e.g., ethyl cellulose, hydroxypropyl cellulose, hydroxypropyl methyl cellulose, microcrystalline cellulose), cellulose esters (e.g., cellulose acetate, cellulose acetate phthalate, hydroxypropyl methyl cellulose phthalate), polyacrylates derivatives, polymethacrylates derivatives, poloxamers, and starch and its derivatives.

In certain embodiments, the hydrophobic matrix may be a hydrophobic wax material. The hydrophobic wax matrix may be any wax-like material suitable for use with the active ingredient. Examples of suitable hydrophobic waxes include, but are not limited to, ceresine wax, beeswax, ozokerite, microcrystalline wax, candelilla wax, montan wax, carnauba wax, paraffin wax, cauassu wax, Japan wax, and Shellac wax.

In certain embodiments of the present composition employing a hydrophobic wax matrix, the microspheres further comprise a densifier. A densifier may used to increase the density of a particle. For example, a densifier may be used to make a particle heavier so that it will approach or be closer to the density of a liquid vehicle in which the microspheres may be suspended. Examples of suitable densifiers include, but are not limited to, titanium dioxide, calcium phosphate, and calcium carbonate. In one embodiment, the one or more densifiers may be present in the microspheres in an amount in the range of from about 0% to about 40% by weight of the microspheres.

The hydrophobic matrix may be present in the microspheres in an amount in the range of from about 5% to about 90%, about 5% to about 30%, about 20% to about 80%, or about 40% to about 60% by weight of the microcapsule. In another embodiment, the hydrophobic matrix may be present in the microcapsule in an amount sufficient to provide sustained release of the active ingredient over a period ranging between about 1 hour to about 12 hours or more. For example, the wax may be present in the microspheres in an amount sufficient to provide sustained release of the hydrophilic active ingredient over a period of about 1 hour, 2 hours, 4 hours, 6 hours, 8 hours, 10 hours, 12 hours, 18 hours, 24 hours, or longer. In certain embodiments, the hydrophobic matrix may be increased or decreased depending on the particular release characteristics desired. In addition, more than one hydrophobic matrix layer may be used to achieve the particular sustained release desired. In general, higher hydrophobic matrix concentrations favor longer, more sustained release of the active ingredient and lower concentrations favor faster, more immediate release.

In certain embodiments, the microspheres of the present disclosure comprise a stabilizer. The stabilizer may improve the properties of the hydrophobic wax matrix and provide improved stability of the microspheres over time, as well as improved dissolution profiles. Changes in microspheres can occur over time that affect the particle's performance. Such changes include physical, chemical, or dissolution instability. These changes are undesirable as they can affect a formulation's shelf stability, dissolution profile, and bioavailability of the active ingredient. For example the hydrophobic wax matrix or active ingredient may relax into a lower energy state, the particle may become more porous, and the size and interconnectivity of pores may change. Changes in either the active ingredient or hydrophobic wax matrix may affect the performance of the particle. The present disclosure is based, at least in part, on the observation that a stabilizer added to the hydrophobic wax matrix improves the stability and performance of the microspheres of the present disclosure. By way of explanation, and not of limitation, it is believed that the stabilizer interacts with the hydrophobic wax material making it resistant to physical changes. Accordingly, the microspheres of the present disclosure comprise a stabilizer. Examples of suitable stabilizers include but are not limited to, cellulose, ethyl cellulose, hydroxyproylmethyl cellulose, microcrystalline cellulose, cellulose acetate, cellulose phthalate, methyl cellylose, chitin, chitosan, pectin, polyacrylates, polymethacrylates, polyvinyl acetate, Elvax® EVA resins, acetate phthalate, polyanhydrides. polyvinylalcohols, silicone elastomers, and mixtures thereof. Stabilizers may be used alone or in combination. The stabilizer may be present in the microspheres in an amount from about 0.1% to about 10% by weight of the particle. For example, the stabilizer may be present in an amount from about 0.1% to about 5%, about 0.5% to about 2.5%, and about 5% to about 10% by weight of the particle.

In certain embodiments, the microspheres of the present disclosure also comprise a release modifier. The present disclosure is also based on the observation that a release modifier improves the performance of hydrophobic wax matrix microspheres particularly during the later stages of the active ingredient's release. The release modifier is believed also to interact with the stabilizer (e.g., improve the stabilizer's solubility) to facilitate preparation of the microspheres. It is also believed that the release modifier may adjust the relative hydrophobicity of the hydrophobic wax material. Examples of suitable release modifiers include but are not limited to, stearic acid, sodium stearate, magnesium stearate, glyceryl monostearate, cremophor (castor oil), oleic acid, sodium oleate, lauric acid, sodium laurate, myristic acid, sodium myristate, vegetable oils, coconut oil, mono-, di-, tri-glycerides, stearyl alcohol, span 20, span 80, and polyethylene glycol (PEG). Release modifiers may be used alone or in combination. For example, in certain embodiments, the release modifier may be a combination of stearic acid and glyceryl mono stearate. The release modifier may be present in the microspheres in an amount from about 0.5% to about 90% by weight of the particle. For example, the release modifier may be present in an amount from about 0.5% to about 10%, about 1% to about 5%, about 2.5% to about 5%, about 5% to about 10%, about 10% to about 25%, about 20% to about 90%, about 40% to about 80%, about 50% to about 70%, about 60% to about 80%, and about 80% to about 90% by weight of the particle. In general, higher release modifier concentrations favor faster release of the active ingredient and lower concentrations favor longer, sustained release.

Moreover, in certain embodiments, the microspheres used in the present compositions can have a particle size diameter of less than 150 µm, less than 100 µm, less than 50 µm, and more preferably for use in intratympanic injections, the microspheres can have a particle size diameter of about 30 µm to about 60 µm. Thus, the compositions of the present invention, in certain embodiments, comprise a plurality of microspheres having a mean particle diameter of less than 150 μm, less than 100 μm, less than 50 μm, and more preferably for use in intratympanic injections, the microspheres can have a particle size diameter of about 30 μm to about 60 μm.

Figure 2:
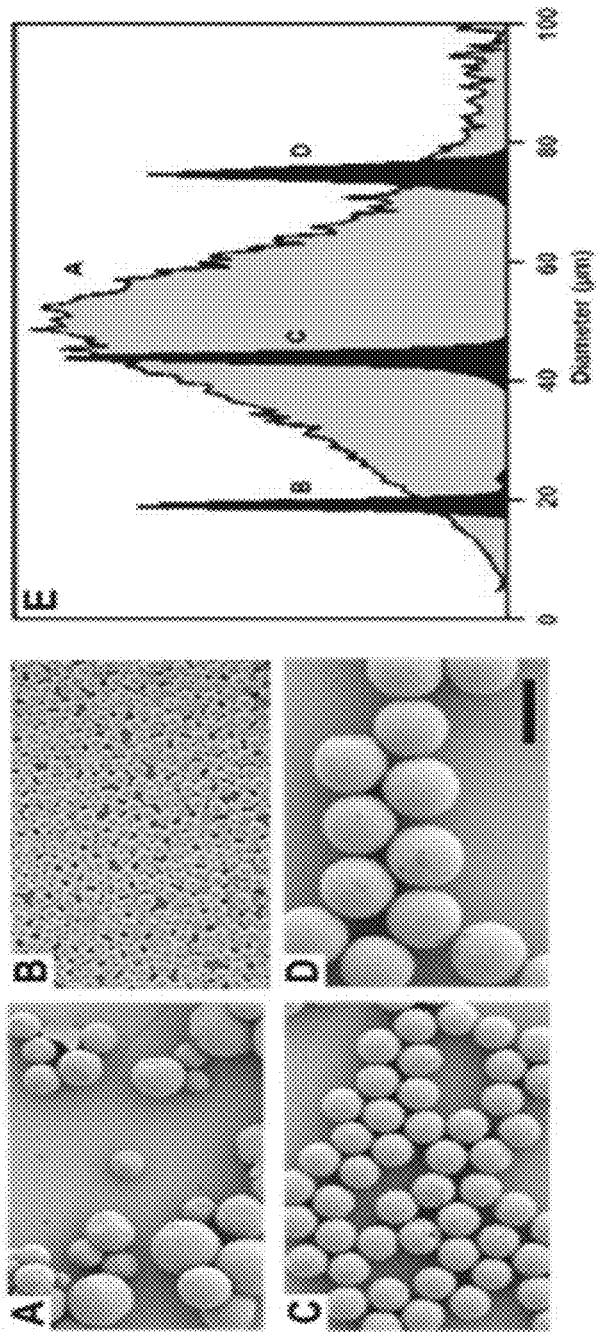
FIG. 2 shows (A) scanning electron micrographs of microspheres formed from emulsion methods, compared to (B,C,D) discrete sizes made by precision particle fabrication technology, and (E) the relative size distribution of precision particle fabrication technology compared to emulsion methods whereas 90% of the PPF-produced microspheres (B-D) are within 2% of mean diameter (Scale bar=100 µm).

The size and size uniformity of drug-encapsulated microspheres directly controls their release profiles. Very small particles (<5 μm or so), often called "fines", release drug quickly, leading to an initial "burst" release effect. Very large particles (>500 μm), on the other hand, tend to slowly release drug over a prolonged period of time. Polydisperse mixtures of drug-encapsulated particles, therefore, offer poor control of drug release. The Precision Particle Fabrication technology produces uniform microspheres that allow for precise control of release properties. Thus, the microspheres of the present composition may possess a particle size distribution that deviates from the mean particle diameter by 10% or less, by 5% or less, or by 2% or less as shown in FIG. 2 (panels B, C, D, and E). Comparatively, other encapsulation methods, including precipitation, phase separation, and/or emulsion technique (panel A) demonstrate standard deviations equal to 25-50% or more of the mean as shown in panel E of FIG. 2.

One exemplary composition of the present disclosure is provided for delivering at least 1.0 μg of a biologically-active compound to the RWM over 30 days. Here, the FFA is 10% w/v Poly(vinyl alcohol)(Mw: 20,000-30,000, 88% hydrolyzed), the surfactant is 5.0% w/v Tween 80, and the biolgocially-active agent is betamethasone. The betamethasone is loaded in microspheres (approximately 30 μm particle size) using the PPF method at any one of the following loading and particle concentrations in a 2 μL total composition volume: (1) 10 mg/ml particle concentration with a particle loading of 5.0% betamethasone; (2) 50 mg/ml particle concentration with a particle loading of 1.0% betamethasone; and (3) 100 mg/ml particle concentration with a particle loading of 0.5% betamethasone. Other specific formulations of the present compositions are presented in the examples below.

Thus, in one embodiment, an injectable composition is provided. The injectable composition of the present embodiment comprises a means for forming a film on a biological tissue. The means comprises a soluble polymer and a carrier liquid, wherein the soluble polymer is from 0.5% to about 10% w/v of the composition, and wherein the carrier liquid is able to evaporate at 37° C. The composition further comprises a biologically-active agent. The composition may further comprise an excipient, wherein the excipient is from about 0.5 to about 5% w/v of the composition.

In certain embodiments, the soluble polymer is selected from the group consisting of polyvinyl alcohol (PVA), polyvinyl acetate (PVAc), alginate, polyethylene glycol (PEG), hydroxypropyl methyl cellulose (HPMC), polyvinyl pyrrolidone (PVP), eudragits, collagen, and gelatin.

In certain embodiments, the carrier liquid is selected from the group consisting of water, ethanol, benzyl alcohol, and ethyl acetate.

In certain embodiments, the excipient is a surfactant selected from the group consisting of polysorbate 20, polysorbate 60, polysorbate 80 or sorbitan laurate.

In certain embodiments, the biologically-active agent is selected from the group consisting of a steroid, an antibody, a peptide, a nucleic acid, an antioxidant, and a small molecule. In certain embodiments, the biologically-active agent is betamethasone or dexamethasone.

In certain embodiments, the injectable composition further comprises a microsphere, wherein the biologically-active agent is present in the microsphere. The microsphere further comprises a material selected from selected from the group consisting of poly (D,L-lactic-co-glycolic acid) (PLGA), poly(lactic acid) (PLA), poly(glycolic acid) (PGA), poly(caprolactone) (PCL), poly(ethylene glycol) (PEG), poly(vinyl acetate) (PVAc), and ethyl cellulose.

In certain embodiments, the microspheres of the present composition possess a mean particle diameter of less than 150 μm, less than 100 μm, less than 50 μm, and in some instances, from about 30 μm to about 60 μm. In certain embodiments, 90% of the microspheres of the composition comprise a particle diameter that does not deviate from the mean particle diameter by more than 10%, 5%, or 2%.

A single-injection method for administration of a composition of the present disclosure to a biological barrier structure is also provided. The method can be performed using any of the above-described compositions. The composition can be loaded in a syringe or catheter. Due to the small particle sizes (30 μm) that can be generated using the PPF technology, syringe gauges of 28 and 30 can be used. In one embodiment, a method for administration of an extended-release therapeutic is provided. The method comprises injecting one of the compositions described herein onto a biological barrier structure and allowing the composition to form a film on the biological barrier structure. In a specific embodiment, a method of treating disorders of the inner ear is provided. In this embodiment, intratympanic injection is accomplished with standard out-patient steroid solution administration techniques, requiring minimal extra effort on the part of physicians and patients. The composition is injected onto the surface of the RWM where it forms a film following evaporation of the water or other solvent used to carry the composition. The film allows the therapeutic, for example, betamethasone, to be retained at the RWM for extended periods of time thereby providing a single injection method for long-term administration of the therapeutic to the inner ear.

In certain instance, the method may further comprise the step of maintaining the subject in a position during the injection and for a time period following the injection sufficient to permit the composition to form a film on the round window membrane. In certain embodiments, the subject is suffering from SSNHL. In instances where the method is performed on a subject suffering from SSNHL, examples of biologically-active agents include, but are not limited to steroids such as betamethasone or dexamethasone, antioxidants such as vitamin A, vitamin C, and vitamin E, and nucleic acids such as siRNA directed to reduce expression of genes that restrict hair cell proliferation and other gene targets that otherwise would prevent regeneration of hair cells as well as gene therapies that would promote hair cell regeneration.

EXAMPLES

The examples herein are illustrations of various embodiments of the present invention and are not intended to limit it in any way.

Example 1

In Vivo Analysis of FFA: Localization and Inflammatory Response

Figure 3:
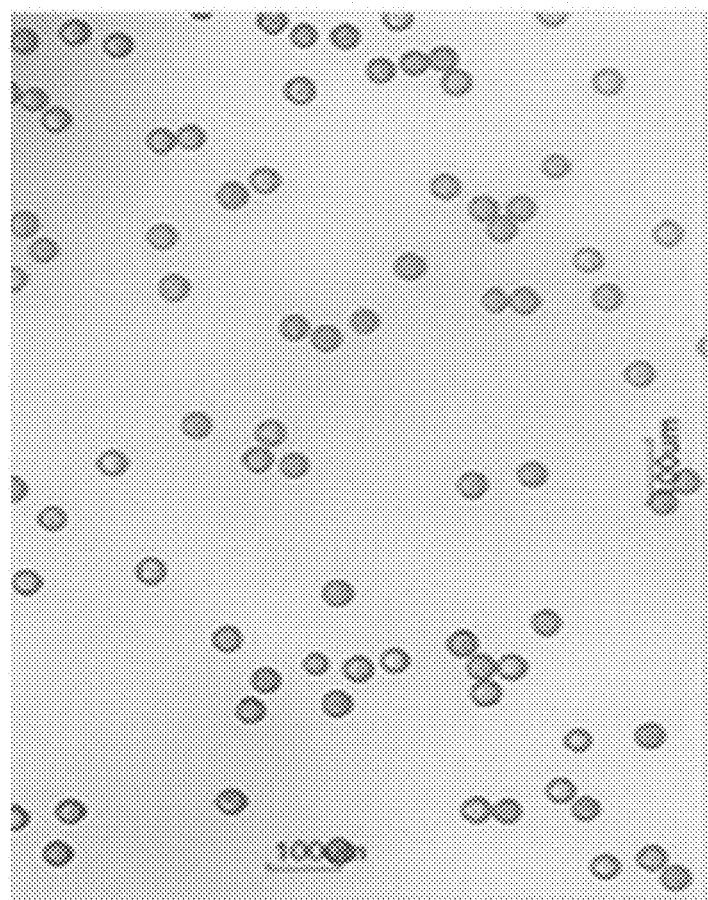
FIG. 3 shows betamethasone-loaded PLGA microspheres created with precision particle fabrication technology with a size of approximately 30 µm.

Uniform betamethasone-loaded biodegradable microspheres were prepared using the Precision Particle Fabrication technology. Briefly, betamethasone was dissolved in dichloromethane (DCM), to which a 50:50 poly (D,L-lactic-co-glycolic acid) (PLGA) was added such that the betamethasone comprised 1.0% w/w of the total solids content. The suspension was loaded into a syringe pump and used to produce microspheres using the Precision Particle Fabrication (PPF) nozzle. The microspheres were collected in a solution of poly (vinyl alcohol) in deionized (DI) water. Following a 3-hour solvent evaporation step, the particles were filtered and lyophilized for 48 hours. The resulting particles are shown in FIG. 3.

Betamethasone-loaded microspheres suspended in the FFA were delivered to mice RWM as follows. C57/BL6 mice were anesthetized with a Ketamine/Xylazine cocktail, laid on their side, and immobilized. The skin and soft tissue was retracted, and an access hole to the tympanic cavity was created with a 28 GA needle. ~2.0 μL injections of 50 mg/mL fluorescent dye-loaded microspheres were then delivered directly above the RWM with a 10 μL Hamilton syringe. The mice were kept in this position for 5 minutes before being sutured and imaged on an IVIS in vivo Imaging System (Perkin-Elmer, Waltham Mass.) to confirm localization of the formulation to the inner ear space, and brought out of anesthesia. Negative control mice were injected with fluorescent microspheres without the FFA component (saline vehicle). At 21 and 35 days timepoints, mice were sacrificed and necropsy was performed to evaluate microsphere localization.

To measure potential inflammatory response, mice were euthanized at 28 days, and the inner ear anatomy was isolated, removed, decalcified, and paraffin-embedded. Samples were sectioned and immunohistochemically stained for two major inflammatory markers, interleukin (IL)-6 and tumor necrosis factor (TNF)-α, in addition to hematoxylin and eosin (H&E). In vitro dissolution testing of betamethasone-loaded microspheres demonstrated that microsphere size plays a role in controlling the release of drug from the microspheres.

Figure 4:
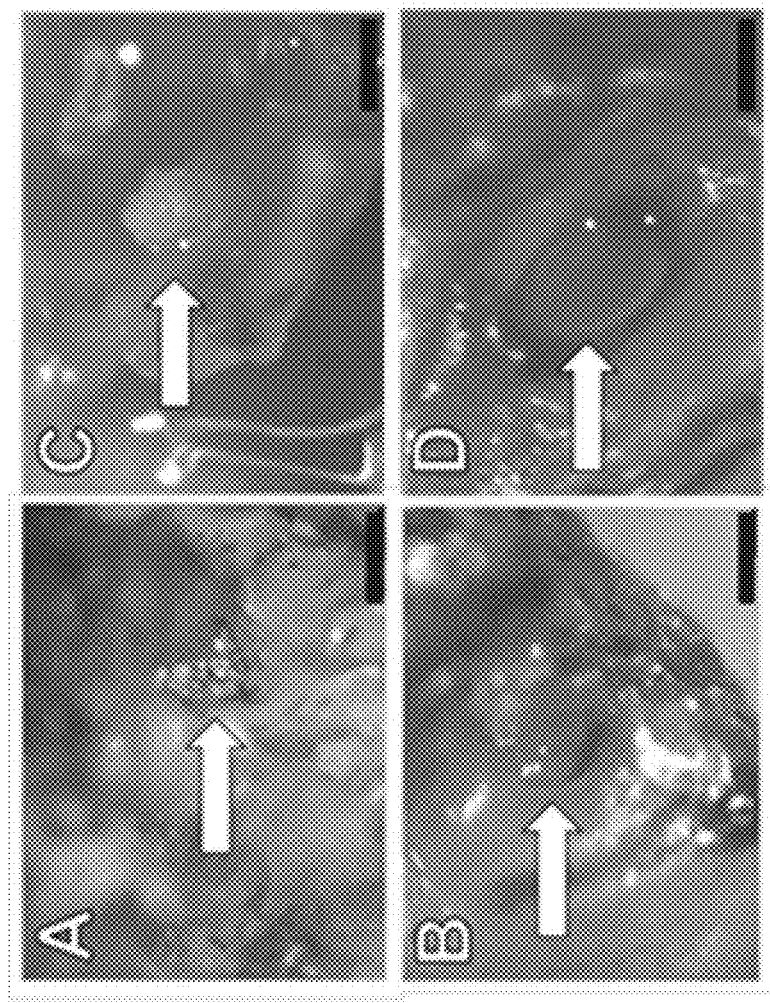
FIG. 4 shows that microspheres with film forming agent are adhered to the RWM at (A) 21 and (C) 35 days post-injection, whereas microspheres injected without a film forming component (i.e. only normal saline) are not present on the RWM at (B) 21 or (D) 35 days post-injection. Scalebar=(A, B) 400 µm and (C, D)=300 µm.

Referring now to FIG. 4, mice treated with microspheres suspended in the FFA had microspheres localized directly on the RWM at 21 days with a thin film as intended (panel A). There appeared to be only a slight loss of sphericity, indicating that some degradation of the particles occurred, but the overall integrity of the delivery system was maintained. Negative control mice displayed no visible microspheres, indicating that the particles had migrated away from the surgical site due to lack of an FFA component (panel B). Similarly, at 35 days, an analogous set of mice were euthanized and dissected. Once again, we were able to see a deposition of microspheres in the space directly adjacent to the RWM in mice treated with microspheres suspended in the FFA (panel C), and an absence of microspheres in negative control mice (panel D).

Figure 5:
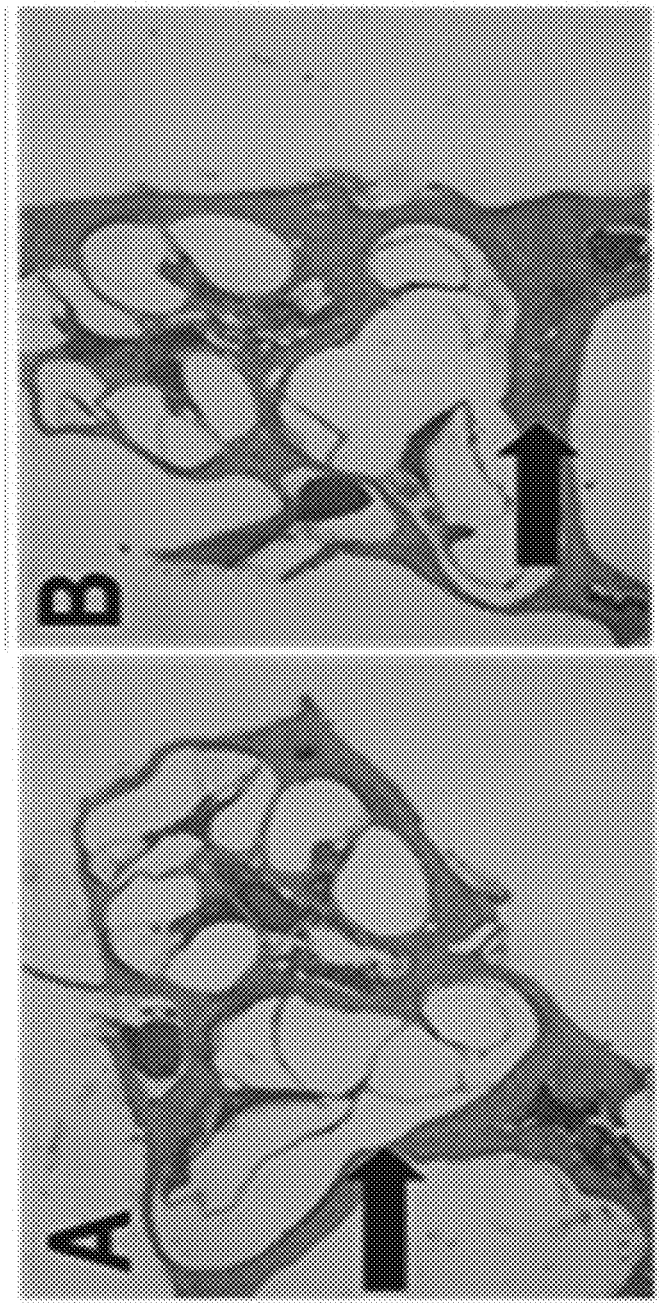
FIG. 5 shows histological staining of the RWM surrounding tissue for the inflammatory protein tumor necrosis factor (TNF) alpha. Staining intensity indicates that no significant inflammatory response was present in mice (A) with the with film forming formulation compared to (B) without the film forming formulation.

Staining indicated that the microspheres and FFA caused no significant inflammatory response. The intensity of TNF-α and IL-6 development was similar between the groups (data not shown), and H&E revealed no discernible changes in hair cell anatomy or apparent tissue reaction as shown in FIG. 5, panels A and B.

Suspending betamethasone-loaded microspheres a film forming agent provided an injectable, extended release intratympanic delivery system that can localize drug to the RWM of mice for greater than 35-days with minimal inflammatory response.

Example 2

Figure 6:
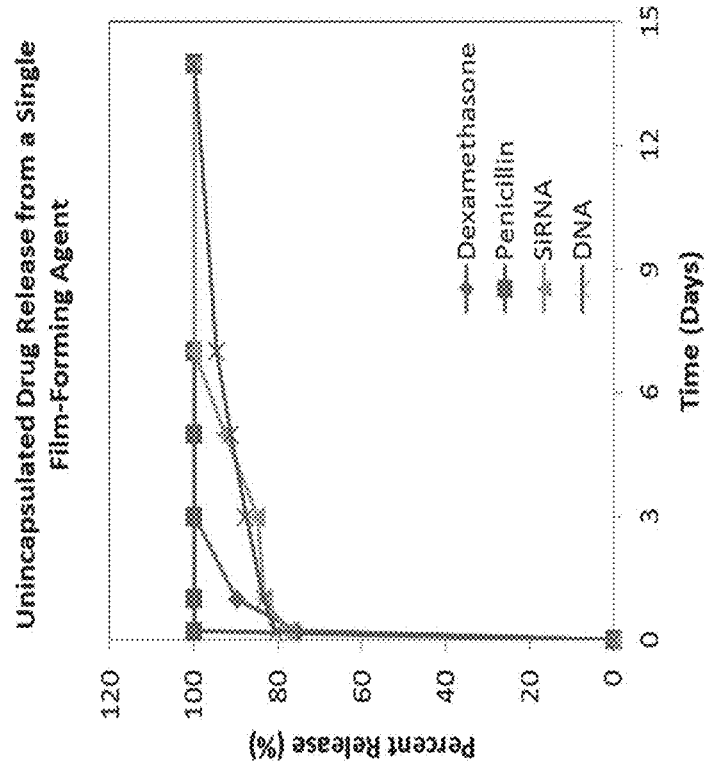
FIG. 6 demonstrates release profiles for various active ingredients in a common film forming agent without encapsulation of the active ingredient.

Various Pharmaceutical Ingredient Release from One Film-Forming Agent (FFA) Type This example illustrates how one film-forming agent type can accommodate release of many pharmaceutical ingredients, without the need for a microsphere component. They are displayed in FIG. 6.

Dexamethasone

An FFA was made, consisting of 10% w/v poly(vinyl alcohol) and 5% v/v Tween 80 dissolved in deionized water. Dexamethasone was dispersed within the film forming agent via sonication at a concentration of 1 mg/mL. On a Franz cell apparatus fitted with a cellulose acetate membrane and 5% w/v Brij O20 receptor phase, 1.0 mL of the dexamethasone/FFA was deposited. Drug diffusion across the membrane at 37° C. was measured for 14 days, and quantified with HPLC. The drug release was normalized to total detected dexamethasone at 14 days.

Penicillin

An FFA was made, consisting of 10% w/v poly(vinyl alcohol) and 5% v/v Tween 80 dissolved in deionized water. Penicillin was dispersed within the film forming agent via sonication at a concentration of 1 mg/mL. On a Franz cell apparatus fitted with a cellulose acetate membrane and 5% w/v Brij O20 receptor phase, 1.0 mL of the penicillin/FFA was deposited. Drug diffusion across the membrane at 37° C. was measured for 14 days, and quantified with HPLC. The drug release was normalized to total detected penicillin at 14 days.

siRNA

An FFA was made, consisting of 10% w/v poly(vinyl alcohol) and 5% v/v Tween 80 dissolved in deionized water. SiRNA was dispersed within the film forming agent via sonication at a concentration of 1 μg/mL. On a Franz cell apparatus fitted with a cellulose acetate membrane and 5% w/v Brij O20 receptor phase, 1.0 mL of the SiRNA/FFA was deposited. Drug diffusion across the membrane at 37° C. was measured for 14 days, and quantified with a picogreen assay. The drug release was normalized to total detected SiRNA at 14 days.

DNA

An FFA was made, consisting of 10% w/v poly(vinyl alcohol) and 5% v/v Tween 80 dissolved in deionized water. DNA was dispersed within the film forming agent via sonication at a concentration of 1 μg/mL. On a Franz cell apparatus fitted with a cellulose acetate membrane and 5% w/v Brij O20 receptor phase, 1.0 mL of the DNA/FFA was deposited. Drug diffusion across the membrane at 37° C. was measured for 14 days, and quantified with a picogreen assay. The drug release was normalized to total detected DNA at 14 days.

Example 3

Figure 7:
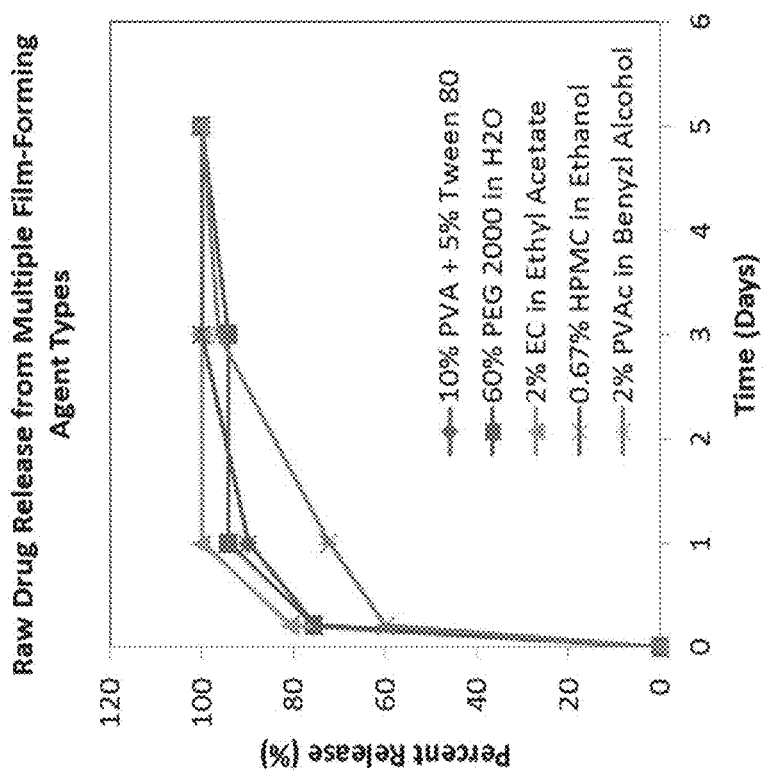
FIG. 7 demonstrates release profiles of dexamethasone from various film forming agent formulations without encapsulation of the dexamethasone.

One Pharmaceutical Ingredient Release from Multiple Film-Forming Agent (FFA) Types This example illustrates how multiple film-forming agent types can accommodate release of a single pharmaceutical ingredient, without the need for a microsphere component. They are displayed in FIG. 7.

10% PVA+5% Tween 80

A FFA was made, consisting of 10% w/v poly(vinyl alcohol) and 5% v/v Tween 80 dissolved in deionized water. Dexamethasone was dispersed within the film forming agent via sonication at a concentration of 1 mg/mL. On a Franz cell apparatus fitted with a cellulose acetate membrane and 5% w/v Brij O20 receptor phase, 1.0 mL of the dexamethasone/FFA was deposited. Drug diffusion across the membrane at 37° C. was measured for 5 days, and quantified with HPLC. The drug release was normalized to total detected dexamethasone at 5 days.
60% PEG 2000 in H2O A FFA was made, consisting of 60% w/v poly(ethylene glycol) 2000 dissolved in deionized water. Dexamethasone was dispersed within the film forming agent via sonication at a concentration of 1 mg/mL. On a Franz cell apparatus fitted with a cellulose acetate membrane and 5% w/v Brij O20 receptor phase, 1.0 mL of the dexamethasone/FFA was deposited. Drug diffusion across the membrane at 37° C. was measured for 5 days, and quantified with HPLC. The drug release was normalized to total detected dexamethasone at 5 days.
2% Ethylcellulose in Ethyl Acetate A FFA was made, consisting of 2% ethylcellulose dissolved in ethyl acetate. Dexamethasone was dispersed within the film forming agent via sonication at a concentration of 1 mg/mL. On a Franz cell apparatus fitted with a cellulose acetate membrane and 5% w/v Brij O20 receptor phase, 1.0 mL of the dexamethasone/FFA was deposited. Drug diffusion across the membrane at 37° C. was measured for 5 days, and quantified with HPLC. The drug release was normalized to total detected dexamethasone at 5 days.
0.67% HPMC in Ethanol A FFA was made, consisting of 0.67% hydroxyproplymethylcellulose (HPMC) dissolved in ethanol. Dexamethasone was dispersed within the film forming agent via sonication at a concentration of 1 mg/mL. On a Franz cell apparatus fitted with a cellulose acetate membrane and 5% w/v Brij O20 receptor phase, 1.0 mL of the dexamethasone/FFA was deposited. Drug diffusion across the membrane at 37° C. was measured for 5 days, and quantified with HPLC. The drug release was normalized to total detected dexamethasone at 5 days.
2% PVAc in Benzyl Alcohol A FFA was made, consisting of 2% poly(vinyl acetate) dissolved in benzyl alcohol. Dexamethasone was dispersed within the film forming agent via sonication at a concentration of 1 mg/mL. On a Franz cell apparatus fitted with a cellulose acetate membrane and 5% w/v Brij O20 receptor phase, 1.0 mL of the dexamethasone/FFA was deposited. Drug diffusion across the membrane at 37° C. was measured for 5 days, and quantified with HPLC. The drug release was normalized to total detected dexamethasone at 5 days.

Example 4

Various Pharmaceutical Ingredient Release from One Microsphere Type

Figure 8:
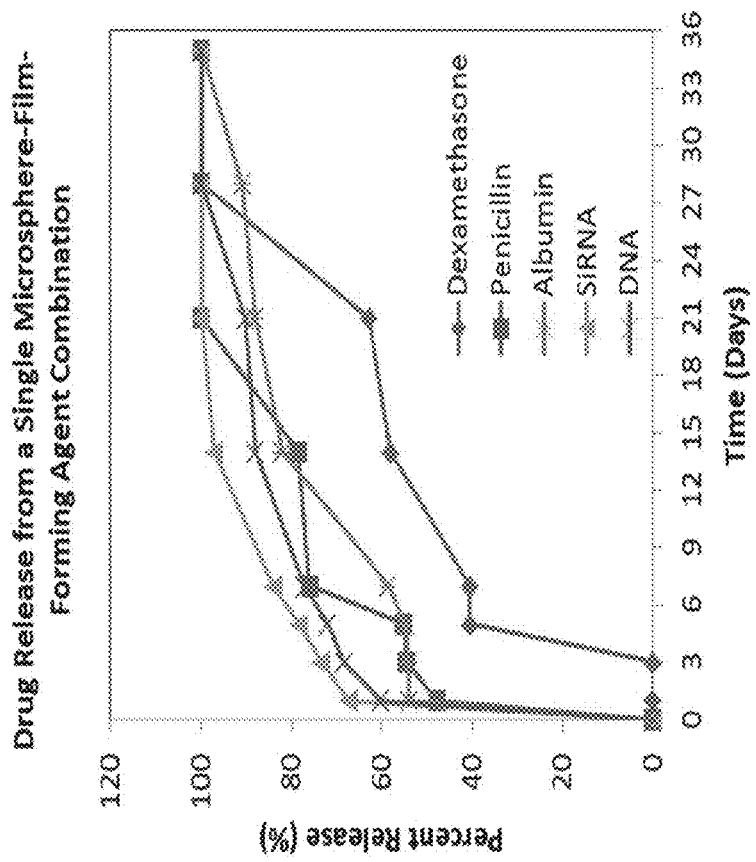
FIG. 8 demonstrates release profiles of various encapsulated active ingredients in a common film forming agent formulation.

The following examples illustrate how one microsphere type can accommodate release of a multiple pharmaceutical ingredients, without the need for a film forming agent component. They are displayed in FIG. 8.
Dexamethasone Dexamethasone was dispersed in a polymer solution consisting of 5050 PLGA (I.V. 0.45 dL/g with ester end group) dissolved in dichloromethane. The drug/polymer solution was processed with precision particle fabrication to make microspheres of ~40 μm, which were collected, filtered, and lyophilized. On a Franz cell apparatus fitted with a cellulose acetate membrane and 5% w/v Brij O20 receptor phase, ~20 mg of the dexamethasone-loaded microspheres were deposited. Drug diffusion across the membrane at 37° C. was measured for 35 days, and quantified with HPLC. Microspheres released approximately 1.7 μg dexamethasone, and the drug release was normalized to total detected dexamethasone at 35 days.
Penicillin Penicillin was dispersed in a polymer solution consisting of 5050 PLGA (I.V. 0.45 dL/g with ester end group) dissolved in dichloromethane. The drug/polymer solution was processed with precision particle fabrication to make microspheres of ~40 μm, which were collected, filtered, and lyophilized. On a Franz cell apparatus fitted with a cellulose acetate membrane and 5% w/v Brij O20 receptor phase, ~20 mg of the penicillin-loaded microspheres were deposited. Drug diffusion across the membrane at 37° C. was measured for 35 days, and quantified with HPLC. Microspheres released approximately 77 μg penicillin, and the drug release was normalized to total detected penicillin at 35 days.
Albumin Albumin was dissolved in water, then dispersed by sonication into a polymer solution consisting of 5050 PLGA (I.V. 0.45 dL/g with ester end group) dissolved in dichloromethane. The protein/polymer solution was processed with precision particle fabrication to make microspheres of ~40 μm, which were collected, filtered, and lyophilized. On a Franz cell apparatus fitted with a cellulose acetate membrane and 5% w/v Brij O20 receptor phase, ~20 mg of the albumin-loaded microspheres were deposited. Protein diffusion across the membrane at 37° C. was measured for 35 days, and quantified with a micro-BCA assay. Microspheres released approximately 4.9 mg albumin, and the protein release was normalized to total detected albumin at 35 days.
SiRNA SiRNA was dissolved in water, then dispersed by sonication into a polymer solution consisting of 5050 PLGA (I.V. 0.45 dL/g with ester end group) dissolved in dichloromethane. The nucleic acid/polymer solution was processed with precision particle fabrication to make microspheres of ~40 μm, which were collected, filtered, and lyophilized. On a Franz cell apparatus fitted with a cellulose acetate membrane and 5% w/v Brij O20 receptor phase, ~20 mg of the SiRNA-loaded microspheres were deposited. Nucleic acid diffusion across the membrane at 37° C. was measured for 35 days, and quantified with a picogreen assay. Microspheres released approximately 1.1 μg, and the nucleic acid release was normalized to total detected SiRNA at 35 days.
DNA DNA was dissolved in water, then dispersed by sonication into a polymer solution consisting of 5050 PLGA (I.V. 0.45 dL/g with ester end group) dissolved in dichloromethane. The nucleic/polymer solution was processed with precision particle fabrication to make microspheres of ~40 μm, which were collected, filtered, and lyophilized. On a Franz cell apparatus fitted with a cellulose acetate membrane and 5% w/v Brij O20 receptor phase, ~20 mg of the DNA-loaded microspheres were deposited. Nucleic acid diffusion across the membrane at 37° C. was measured for 35 days, and quantified with a picogreen assay. Microspheres released approximately 1.4 μg, and the nucleic acid release was normalized to total detected DNA at 35 days.

Example 5

Figure 9:
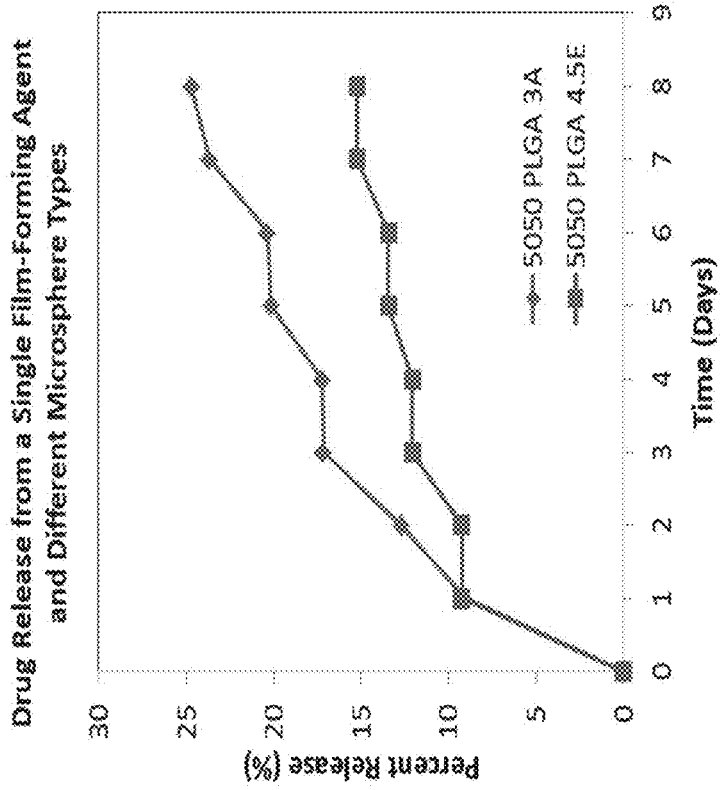
FIG. 9 demonstrates release profiles of betamethasone encapsulated in two different microsphere types in a common film forming agent formulation.

One Pharmaceutical Ingredient Release from Different Microsphere Types in a Single Film-Forming Agent Type This example illustrates how different microsphere types can change release of a single pharmaceutical ingredient, without the need for changing the film forming agent component. They are displayed in FIG. 9.

5050 PLGA 3A

Betamethasone was dispersed in a polymer solution consisting of 5050 PLGA (I.V. 0.30 dL/g with acid end group) dissolved in dichloromethane. The drug/polymer solution was processed with precision particle fabrication and the microspheres were collected, filtered, and lyophilized. On a Franz cell apparatus fitted with a cellulose acetate membrane and 5% w/v Brij 020 receptor phase, ~10 mg of the betamethasone-loaded microspheres were suspended in 100 uL of 10% w/v poly(vinyl alcohol) and 5% v/v Tween 80 film-forming agent and deposited. Drug diffusion across the membrane at 37° C. was measured for 8 days, and quantified with HPLC. The drug release was normalized to total entrapped drug, which was approximately 0.75% w/w of the microspheres.

5050 PLGA 4.5E

Betamethasone was dispersed in a polymer solution consisting of 5050 PLGA (I.V. 0.45 dL/g with ester end group) dissolved in dichloromethane. The drug/polymer solution was processed with precision particle fabrication and the microspheres were collected, filtered, and lyophilized. On a Franz cell apparatus fitted with a cellulose acetate membrane and 5% w/v Brij 020 receptor phase, ~10 mg of the betamethasone-loaded microspheres were suspended in 100 uL of 10% w/v poly(vinyl alcohol) and 5% v/v Tween 80 film-forming agent and deposited. Drug diffusion across the membrane at 37° C. was measured for 8 days, and quantified with HPLC. The drug release was normalized to total entrapped drug, which was approximately 0.38% w/w of the microspheres.

Example 6

Figure 10:
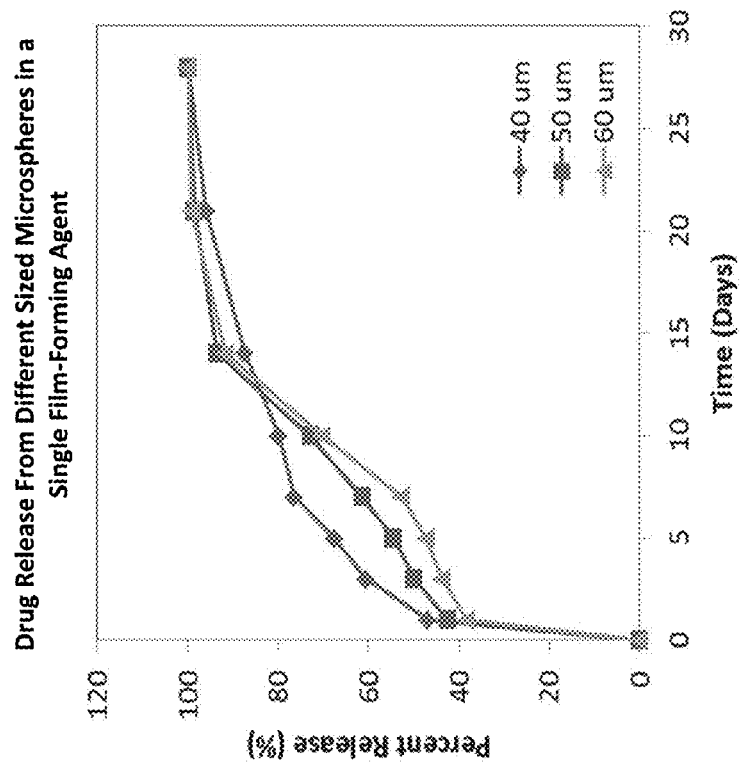
FIG. 10 demonstrates release profiles of betamethasone encapsulated in three different sizes of microspheres in a common film forming agent formulation.

One Pharmaceutical Ingredient Release from Different Microsphere Sizes in a Single Film-Forming Agent Type This example illustrates how different microsphere sizes can change release of a single pharmaceutical ingredient, without the need for changing the film forming agent component or microsphere material chemistry. They are displayed in FIG. 10.

40 μm

Betamethasone was dispersed in a polymer solution consisting of 5050 PLGA (I.V. 0.30 dL/g with acid end group) dissolved in dichloromethane. The drug/polymer solution was processed with precision particle fabrication to make microspheres of ~40 μm, which were collected, filtered, and lyophilized. On a Franz cell apparatus fitted with a cellulose acetate membrane and 5% w/v Brij O20 receptor phase, ~10 mg of the betamethasone-loaded microspheres were suspended in 100 uL of 10% w/v poly(vinyl alcohol) and 5% v/v Tween 80 film-forming agent and deposited. Drug diffusion across the membrane at 37° C. was measured for 28 days, and quantified with HPLC. Microspheres contained approximately 0.38% w/w betamethasone, and the drug release was normalized to total detected betamethasone at 28 days.

50 μm

Betamethasone was dispersed in a polymer solution consisting of 5050 PLGA (I.V. 0.30 dL/g with acid end group) dissolved in dichloromethane. The drug/polymer solution was processed with precision particle fabrication to make microspheres of ~50 μm, which were collected, filtered, and lyophilized. On a Franz cell apparatus fitted with a cellulose acetate membrane and 5% w/v Brij O20 receptor phase, ~10 mg of the betamethasone-loaded microspheres were suspended in 100 uL of 10% w/v poly(vinyl alcohol) and 5% v/v Tween 80 film-forming agent and deposited. Drug diffusion across the membrane at 37° C. was measured for 28 days, and quantified with HPLC. Microspheres contained approximately 0.65% w/w betamethasone, and the drug release was normalized to total detected betamethasone at 28 days.

60 μm

Betamethasone was dispersed in a polymer solution consisting of 5050 PLGA (I.V. 0.30 dL/g with acid end group) dissolved in dichloromethane. The drug/polymer solution was processed with precision particle fabrication to make microspheres of ~60 μm, which were collected, filtered, and lyophilized. On a Franz cell apparatus fitted with a cellulose acetate membrane and 5% w/v Brij O20 receptor phase, ~10 mg of the betamethasone-loaded microspheres were suspended in 100 uL of 10% w/v poly(vinyl alcohol) and 5% v/v Tween 80 film-forming agent and deposited. Drug diffusion across the membrane at 37° C. was measured for 28 days, and quantified with HPLC. Microspheres contained approximately 0.69% w/w betamethasone, and the drug release was normalized to total detected betamethasone at 28 days.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

While compositions and methods are described in terms of "comprising," "containing," or "including" various components or steps, the compositions and methods can also "consist essentially of" or "consist of" the various components and steps.

All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method for providing an extended-release treatment to a subject, the method comprising injecting a composition onto a biological tissue of the subject suffering from sensorineural hearing loss no more than one time in a 14 day period, wherein the composition comprises a biologically-active agent dispersed in a film-forming agent, wherein the film-forming agent comprises water and polyvinyl alcohol (PVA), wherein the PVA is from about 5% to about 10% w/v of the film-forming agent, wherein the PVA has a molecular weight of 20,000 to 30,000 Daltons, wherein the film-forming agent is free of solvent.

2. The method of claim 1 further comprising the step of maintaining the subject in a fixed position following injection until the composition forms a film on the biological tissue.

3. The method of claim 1, wherein the biological tissue is the middle ear.

4. The method of claim 1, wherein the biological tissue is the round window membrane of the inner ear.

5. The method of claim 1, wherein the step of injecting the composition is performed by an intratympanic injection.

6. The method of claim 1, wherein the biological tissue is the middle ear, and wherein the biologically-active agent is a therapeutic compound used in the treatment of sensorineural hearing loss.

7. The method of claim 1, wherein the composition further comprises a surfactant, wherein the surfactant is from about 0.5% to about 5% w/v of the film-forming agent.

8. The method of claim 7, wherein the surfactant is selected from the group consisting of polysorbate 20, polysorbate 60, polysorbate 80 or sorbitan laurate.

9. The method of claim 7, wherein the PVA is about 10% w/v of the film-forming agent and the surfactant is about 5% w/v of the composition.

10. The method of claim 1 wherein the PVA is about 88% hydrolyzed.

11. A method for providing an extended-release treatment to a subject, the method comprising injecting a composition onto a middle ear tissue of the subject no more than one time in a 14 day period, wherein the composition comprises a biologically-active agent dispersed in a film-forming agent, wherein the film-forming agent comprises water and polyvinyl alcohol (PVA), wherein the PVA is from about 5% to about 10% w/v of the film-forming agent, wherein the PVA has a molecular weight of 20,000 to 30,000 Daltons, and wherein the film-forming agent is free of solvent.

12. A method for providing an extended-release treatment to a subject, the method comprising injecting a composition onto a biological tissue of the subject no more than one time in a 14 day period, wherein the step of injecting the composition is performed by an intratympanic injection, wherein the composition comprises a biologically-active agent dispersed in a film-forming agent, wherein the film-forming agent comprises water and polyvinyl alcohol (PVA), wherein the PVA is from about 5% to about 10% w/v of the film-forming agent, wherein the PVA has a molecular weight of 20,000 to 30,000 Daltons, and wherein the film-forming agent is free of solvent.

* * * * *